US00RE38407E

(19) United States
(12) Reissued Patent
Mezel et al.

(10) Patent Number: US RE38,407 E
(45) Date of Reissued Patent: Jan. 27, 2004

(54) PAIN MANAGEMENT WITH LIPOSOME-ENCAPSULATED ANALGESIC DRUGS

(75) Inventors: Michael Mezel, Nova Scotia (CA); Orlando Hung, Nova Scotia (CA)

(73) Assignee: Delex Therapeutics Inc., Mississauga (CA)

(21) Appl. No.: 09/880,054

(22) Filed: Jun. 14, 2001

Related U.S. Patent Documents

Reissue of:
(64) Patent No.: 5,451,408
Issued: Sep. 19, 1995
Appl. No.: 08/216,590
Filed: Mar. 23, 1994

(51) Int. Cl.[7] ..... A61K 9/50
(52) U.S. Cl. ..... 424/450; 424/1.13; 424/1.21; 514/326; 514/329; 514/817
(58) Field of Search ..... 424/1.13, 1.21, 424/450; 514/817, 326, 329

(56) References Cited

U.S. PATENT DOCUMENTS

| | | | | |
|---|---|---|---|---|
| 4,485,054 A | | 11/1984 | Mezei et al. | 264/4.6 |
| 4,761,288 A | | 8/1988 | Mezei | 424/450 |
| 4,937,078 A | | 6/1990 | Mezei et al. | 424/450 |
| 5,049,388 A | * | 9/1991 | Knight et al. | 424/450 |

OTHER PUBLICATIONS

Bangham et al.; *J. Mol. Biol.*, 13:238–252, 1965.
Mezei, *Controlled Release Dosage Forms*, Tipnis (ed), Bombay College of Pharmacy, India, pp. 37–46, 1988.
Meisner et al.; *Proceedings, 15th Int'l Symposium on Controlled Release of Bioactive Materials*, 15:262–263, 1988.
Mezei et al.; *Drug Permeation Enhancement, Theory and Application*, Hsieh (ed), Marcel Dekker Inc., New York, 1993, pp. 171–198.
Gesztes et al.; *Anesth. Analg.* 67:1079–1081, 1988.
Bernards et al.; *Anesthesiology*, 77:529–535, 1992.
Ready, *Anesthesia*, 3rd ed., Miller (ed), Churchill Livingston, New York, 1990, pp. 2135–2146.
Khojasteh et al., *J. Clin. Oncology* 5:956–961, 1987.
Varvel et al.; *Anesthesiology* 70:928–934, 1989.
Worsley et al., *Anaesthesia* 45:449–451, 1990.
Higgins et al., *Anaesthesia* 46:973–976, 1991.
Mihalko et al.; *Liposomes as Drug Carriers*, Gregoriadis (ed), John Wiley & Sons Ltd., Toronto, 1988, pp. 679–694.
Meisner et al.; *J. Microencapsulation* 6:379–387, 1989.
Meisner, *Pharmaceutical Particulate Carriers Therapeutic Application*, Roland (ed), Marcel Dekker Inc., New York 1993, pp. 31–63.
Oyarzun et al.; *An. Rev. Resp. Dis.*, 121:709–721, 1980.
Meyers et al.; *An. Rev. Resp. Dis.*, 141A675, 1990.
Ivey et al.; *Pediatr. Res.,* 11:573, 1977.
Morley et al.; *Lancet*, i:64–68, 1981.
Thomas et al., *Chest*, 99:1268–1270, 1991.

* cited by examiner

*Primary Examiner*—Richard L. Raymond
(74) *Attorney, Agent, or Firm*—Nixon & Vanderhye

(57) ABSTRACT

Liposome-encapsulated opioid analgesic agents delivered by the pulmonary route provide local, or systemic analgesia superior to that produced by the solution form of these agents administered by parentral (intravenous, intramuscular, or subcutaneous injection) or oral routes.

24 Claims, 4 Drawing Sheets

IV
Aerosol
Therapeutic range
Aerosol
IV
Plasma Fentanyl Conc (ng/ml)
10.00
1.00
0.10
0.01
Time (min)
0
200
400
600
800
1000
1200
1400
1600
0
20
40
60
0
1
2
3
4
5

Plasma Alfentanil Conc (ng/ml)
100.00
10.00
1.00
0.10
0.01
0
10
20
30
40
50
Time (hr)
Aerosol
IV IV
Aerosol
50
40
30
20
10
0
0.0
0.5
1.0
1.5
2.0
Time (hr)

PAIN MANAGEMENT WITH LIPOSOME-ENCAPSULATED ANALGESIC DRUGS

Matter enclosed in heavy brackets [ ] appears in the original patent but forms no part of this reissue specification; matter printed in italics indicates the additions made by reissue.

*The present application is a reissue of Ser. No. 08/216,590, filed Mar. 23, 1994.*

BACKGROUND OF THE INVENTION

1. Field of the Invention

The present invention relates to the management of an individual's pain by administering liposome encapsulated opioids to the individual through the pulmonary system.

2. Description of the Related Art

Liposomes are microscopic vesicles composed of an aqueous compartment surrounded by a phospholipid bilayer which acts as a permeable entrapment barrier, for example for drug molecules (Gangham A. D., et al: J Mol Biol: 13:238–252, 1965). There are many types of liposomes that can be used in various routes of drug administration (see a recent review by Gregoriadis (ed.) in Liposome Technology, 2nd edition, vol I–III, CRC Press, Boca Ranto, Fla., 1993). Certain types of liposomes can provide a controlled, sustained release system (Mezei M: In Controlled release dosage forms. Tipnis HP (ed): Bombay College of Pharmacy, India, 1988, pp 37–46). In such a system, the rate of drug release is primarily determined by the liposome's physicochemical properties. Liposomes can be tailored for a specific application by modification of size, composition, and surface charge to provide the desired rate of drug delivery (Meisner D, et al: In Proceedings, 15th International Symposium on Controlled Release of Bioactive Materials. 15:262–263, 1988; Mezei M: In Drug Permeation Enhancement, Theory and Application Hsich DS (ed): Marcel Dekker Inc., New York, 1993, pp 171–198; and Meisner D, et al: J Microencapsulation 6:379–387, 1989). Decades of research in liposome technology has indicated that liposome-encapsulation is an effective and safe drug delivery system.

Liposomes have been used clinically as intravenous drug carrier systems in enzyme replacement therapy (Belchetz P. E., et al: Lancet ii:116–117, 1977), in anti-fungal therapy (Lopez-Gerenstein G, et al: J Infect Dis 151:704–709, 1985), and in chemotherapy (Sculier J. P., et al: J Clin Oncol 4:789–797, 1986). Liposome encapsulation of local anesthetics provides intensified and prolonged action, when applied on the skin (Gesztes and Mezei: Anesth Anag 67: 1079–1081, 1988; Mezei and Gesztes: U.S. Pat. No. 4,973,078, 1990). Liposome-encapsulated alfentanil administered intrathecally produced prolonged spinal anesthesia in rats (Bernards, et al: Anesthesiology, 77:529–535, 1992).

Despite years of therapeutic advances, acute and chronic pain remain major medical problems. Acute pain following surgical procedures has been associated with adverse physiological alterations in the pulmonary (Ford G. T., et al: Am Rev Resp Dis 127:431, 1983), cardiovascular (Ready B: In Anesthesia, 3rd edition, Miller RD (ed), Churchill Livingstone, New York, 1990 pp. 2135–2146), gastrointestinal, urinary (Cousins M: In Textbook of Pain, 2nd Edition, Wall, Melzack (eds): Churchill Livingstone, New York, 1989, pp 284–305.) and neuroendocrine systems (Kehlet H: In Acute Pain Management. Cousin and Phillips (eds): Churchill Livingstone, New York, 1986, pp 49). Many of these undesirable physiological changes can be minimized with effective analgesia (Cousins M: In Textbook of Pain, 2nd Edition. Wall, Melzack (eds): Churchill Livingstone, New York, 1989, pp 284–305). While systemic administration of opiods remains the most common treatment method of acute pain management, their on-demand intermittent intramuscular administration has been shown to be ineffective in managing pain in hospitalized patients (Ready B: In Anesthesia, 3rd edition, Miller RD (ed), Churchill Livingstone, New York, 1990 pp 2135–2146; Cousins M: In Textbook of Pain, 2nd Edition, Wall and Melzack (eds): Churchill Livingstone, New York, 1989, pp 284–305; and Austin K. L., et al: Pain 8:47, 1980). Recent advances in pain management using spinal or epidural administration of opiods provide effective alternatives for acute pain management. However, these analgesic methods are invasive, and are associated with significant complications and costs. Three advances in clinical pharmacology have attempted to address these shortcomings: oral sustained-release opiods, patient-controlled analgesia, and transdermal drug delivery. These three approaches have respective advantages in terms of safety, efficacy, and cost.

Oral sustained-release opiods (e.g. MS CONTIN ™) have provided an effective, and fairly inexpensive, means of administering opiods to patients with chronic pain (Khojasthe A., et al: J Clin Oncology 5:956–61, 1987). Unfortunately, the use of an oral route makes this method unavailable to many hospitalized patients with acute pain who may have gastrointestinal dysfunction from cancer or following surgery (Banning A. M., et al: Anesth Anag 65:385–8, 1986). Additionally, plasma levels obtained from oral preparations show wide variability because of individual variations in tablet dissolution, intragastric pH, intragastric motility, and hepatic first pass metabolism (Khojasthe A., et al: J Clin Oncology 5:956–61, 1987).

Patient-controlled analgesia (PCA) using an infusion pump, has been shown to be effective in providing post-operative analgesia (White P. F.: JAMA 259–243, 1988). The major advantage of this technique is that titration by the patient compensates for pharmacokinetic and pharmacodynamic variability, and thus potentially produces adequate analgesia. Because PCA requires continuous intravenous access and maintenance of both the pump and infusion line, however, this method of analgesia is usually limited to hospitalized patients (Albert J. M., et al: Dis Colon Rectum 31:83–6, 1988). Even so, the major limitation of PCA is cost. The pump, prefilled syringes and specialized tubing that are used with PCA are expensive, as are the personnel required to maintain intravenous access (White P. F.: Anesthesiology 66:81–3, 1987).

Transdermal fentanyl delivery was recently introduced to overcome the shortcomings of oral sustained-release analgesics and PCA. The advantages of such a system are that it is entirely non-invasive and, can maintain a plateau of analgesia for up to three days following application. However, variability in physical properties of the stratum-corneum of the dermis creates more than 50% variability in fentanyl absorption (Varvel J. R., et al: Anesthesiology 70:928–934, 1989). Even though the device was developed using an acute pain model (Caplan R. A., et al: JAMA 261:1036–1039, 1992), the variability is so high that transdermal fentanyl has only been approved for use in cases of chronic pain. Additionally, transdermal fentanyl may not be appropriate for acute post-operative pain management since the drug concentration initially rises very slowly, reaching a plateau 12–16 hours following application of the fentanyl patch. Lastly, the fentanyl patches are expensive. Thus, high variability, slow onset, and moderately high cost all limit the application of transdermal fentanyl (Varvel J. R., et al: Anesthesiology 70:928–934, 1989).

Administration of an opioid, such as fentanyl, through the pulmonary system using a nebulizer has recently been reported for providing postoperative analgenia (Worsley M. H., et al: Anaesthesia 1990, 45:449–451; and Higgins M. J., et al: Anaesthesia 1991, 46:973–976). The duration of analgesia was short due to rapid clearance of fentanyl from the lungs.

Certain liposome-encapsulated drugs administered via the pulmonary route have provided sustained release and, therefore, prolonged drug action (Mihalko P. J., et al: In Liposomes as Drug Carriers, Gregoriadis (ed.), John Wiley & Sons Ltd. Toronto, 1988, pp 679–694; Meisner D., et al: J Microencapsulation 6:379–387, 1989 and Meisner D.: In Pharmaceutical Particulate Carriers: Therapeutic Application. Roland A (ed), Marcel Dekker Inc. New York 1993, pp 31–63). Liposomal drug delivery to the lungs appears to be well tolerated in both animals and humans. In animal models with rabbits and mice, acute and chronic inhalation of liposome aerosol did not adversely affect lung appearance, cell consistency, or pulmonary histopathology (Oyarzum M. J., et al: An Rev Resp Dis 121:709–721, 1980, and Myers M. A., et al: An Rev Resp Dis 141:A675, 1990). No adverse effects have been associated with inhalation of exogenous phospholipids to preterm infants with respiratory distress syndrome (Ivey H., et al: Pediatr Res 11:573, 1977 and Morely C. J., et al: Lancet i:64–68, 1981). Thomas and colleagues (Thomas, et al: Chest 99: 1268–1270, 1991) reported no oxygen desaturation, deterioration in pulmonary function or side effects associated with the inhalation of liposomes in healthy human volunteers.

DESCRIPTION OF THE INVENTION

Figures 1A, 1B:
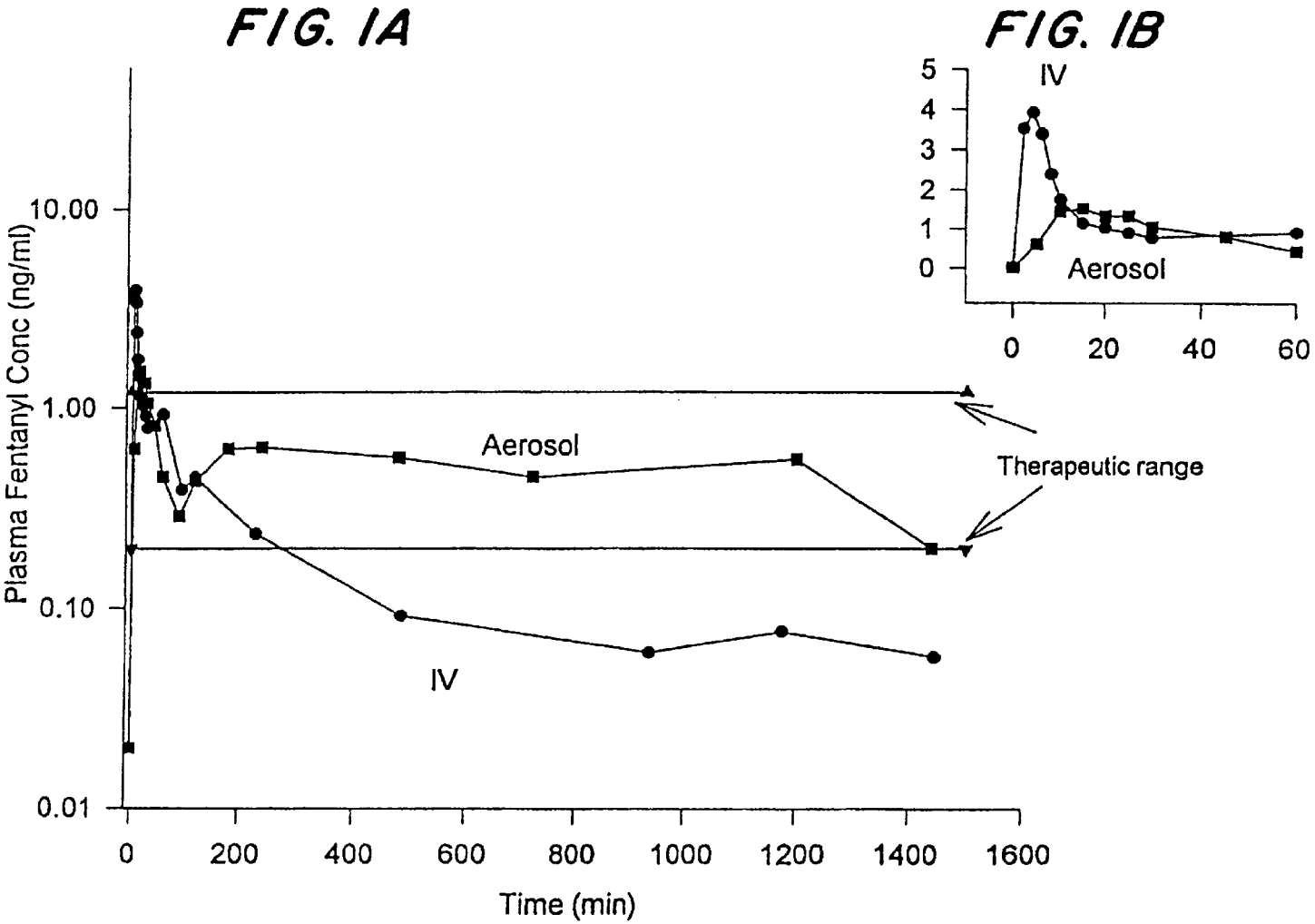
FIGS. 1A and 1B graphically present the plasma fentanyl concentrations versus time resulting from both intravenous administration and inhalation administration as described in Example 9.

The present invention broadly relates to the use of liposome encapsulation to improve the analgesic effects of opioid analgesic agents administered to an individual via the pulmonary system. A major advantage of this invention is the obtainment of a sustained analgesic effect using a noninvasive method of drug delivery. Because of the noninvasive nature of this drug delivery system, it is particularly suitable for certain patient populations, such as small children where other delivery systems are problematic. The present invention may be used to provide systemic analgesic treatment both for human and veterinary purposes. Analgesic agents, such as opioids, are good candidates for liposome encapsulation.

The amount of the opioid analgesic agent or drug to be included in the liposomal preparation is not, per se, critical and can vary within wide limits depending inter alia on the particular agent, the intended application and the lipid used. Generally, the opioid analgesic agent may be included in an amount of between about 0.005 to 10% by wt. of the liposomal preparation and more usually may be included in an amount of between 0.01 and 0.1% by wt.

Inhaled liposome-encapsulated opioid analgesic agents are expected to have less variability than other routes of drug delivery (e.g. transdermal administered fentanyl), will not require a functioning bowel, can provide rapid onset of analgesic action suitable for acute pain management, and will be inexpensive to manufacture. In other words, inhalation of liposome-encapsulated opioid analgesic agents offers the following benefits as a method of analgesic drug administration: (1) a simple and noninvasive route of administration; (2) a rapid onset of analgesia from absorption of free opioid (in the range of 10–20% of the opioid dose); (3) a sustained analgesia from continued release of liposome-encapsulated opioid (approximately 80–90% of the opioid dose) and (4) a low cost. Thus, inhaled liposome-encapsulated fentanyl may provide a significant advance in our therapeutic armamentarium against acute and chronic pain, at lower cost than currently available therapies.

The sustained release property of the liposomal product can be regulated by the nature of the lipid membrane and by the inclusion of other excipients in the composition of the liposomal products. Decades of research in liposome technology permits a reasonable prediction on the rate of drug release based on the composition of the liposome formulation. The rate of drag release is primarily dependent on the nature of the phospholipids, e.g. hydrogenated (—H) or unhydrogenated (—G), or the phospholipid/cholesterol ratio (the higher this ratio, the faster the rate of release), the hydrophilic/lipophilic properties of the active ingredients and by the method of liposome manufacturing.

Materials and procedures for forming liposomes are well-known to those skilled in the art and need not be described herein in detail. Reference is made to U.S. Pat. Nos. 4,485,054, 4,761,288 and 4,937,078, the disclosures of which are hereby incorporated by reference, for the disclosure of suitable liposome preparation techniques. As described therein, the liposomes can be prepared as multilamellar lipid vesicles (MLV), unilamellar lipid vesicles, including small unilamellar vesicles (SUV) and large unilamellar vesicles (LUC) and as multivesicular liposomes. Many other liposome manufacturing techniques also can be used to make the final liposomal product containing the appropriate active ingredient, lipids, and other excipients as will be understood by those skilled in the art. For example, suitable liposomes also can be prepared using the known ethanol or ether injection methods. Suitable active ingredients are opioid analgesic agents including such opioid agents as alfentanil, anileridine, codiene, diamorphine, fentanyl, hydrocodone, hydromorphone, meperidine (pethidine), morphine, oxycodone, oxymorphone, propoxyphene and sufentanil and the opioid agonists and antagonists pentazocine and nalbuphine. Lipid components are usually phospholipids and cholesterol; excipients are tocopherol, antioxidants, viscosity inducing agents, and/or preservatives.

Phospholipids are particularly useful, such as those selected from the group consisting of phosphatidylchloines, lysophosphatidylchloines, phosphatidylserines, phosphatidylethanolamines, and phosphatidylinositols. As noted, such phospholipids often are modified using for example, a modifying agent selected from the group consisting of cholesterols, stearylamines, stearic acid, and tocopherols. The lipid typically is dissolved in a solvent and the solvent then is evaporated, typically under a reduced pressure, to yield a thin lipid film containing any lipophilic analgesic agent. Afterwards, the film is hydrated, with agitation, using an aqueous phase containing any desired electrolytes and any hydrophilic analgesic agent, and lipid vesicles entrapping the analgesic agent are produced. As recognized by those skilled in the art, while certain materials and procedures may give better results with certain drugs, the use of particular materials and procedures are not narrowly critical and optimum conditions can be determined using routine testing. Additionally, as also noted, a preservative or antioxidant often will be added to the preparation.

In summary, the pharmacokinetic profiles of this new noninvasive method of opioid delivery indicate that pulmonary administration of the liposome-encapsulated opioid analgesic agents offers significant advantages over the conventional parenteral opioid administration as a method of analgesic drug administration with rapid onset and sustained analgesic effect.

The liposome-encapsulated opioid analgesic agents normally are administered to a human patient in an amount to provide an accepted and necessary level of therapeutic postoperative analgesic plasma concentration, commonly agreed to be in the range of 0.2 to 1.2 ng/ml. As will be recognized by those skilled in the art, the required amount of encapsulated opioid in a single dose will depend on a variety of factors including inter alia body weight, lung capacity, lung function and the like. Inhalation of between about 1000 $\mu$g to 4000 $\mu$g per dose will be suitable in many cases. Of course, within the broad practice of the present invention the dose amount can be varied as needed to obtain any desired effect.

In accordance with the present invention, the liposome-encapsulated opioid analgesic agents can be delivered by direct inhalation of an aerosol using any of the variety of known methods for delivering drugs through the pulmonary system.

The bioavailability or the amount of drug delivered to the lungs can be improved with the use of a large initial volume of solution placed in the nebulizer, a higher compressed gas flow rate (12 $I.min^{-1}$) to produce a higher percentage of small droplets (1–5$\mu$), deep inhalation with breath holding, and the use of positive expiratory pressure (Resistex ™, D. C. Lung Co. Inc., Sebastopol, Calif., U.S.A.) during the aerosol therapy (Newman S. P.: Chest 88(2):152s–160s, 1985 and Anderson J. B., et al: Eur J Resp Dis 63(suppl) 119:97–100, 1982).

The following examples are illustrated of the present invention, and are not to be regarded as limiting. In the following examples, representative active ingredients: fentanyl, alfentanil, sufentanil and morphine were encapsulated into uni- and multi-lamellar liposomes using a procedure described by Mesei M., et al: U.S. Pat. No. 4,485,054. Briefly, the phospholipids, cholesterol and lipophilic opioid analgesic agents (and other lipid soluble agents, if present in the formula) were dissolved in chloroform/methanol mixture in a pear shape flask containing glass beads. The solvent was then evaporated to dryness in a rotary evaporator under reduced pressure at 30° C. until a smooth, thin lipid film was obtained on the surface of the flask and glass beads. The film was then hydrated with a sterile aqueous solution containing any water soluble (hydrophilic) opioid analgesic agents (this would include most salt forms of the analgesic compounds), at the transition temperature of the phospholipid, by shaking 30 minutes in a Lab Line Orbit Environment-Shaker. The sterile water may contain some electrolytes, e.g., sodium chloride, sodium bicarbonate, and/or calcium chloride in an amount that renders the final product isotonic and yields a pH near 7.4. In the following examples, the ethanol was generally added to the aqueous phase before forming the liposomes or to the finished liposomal product. The liposomes were then separated from the glass beads by filtering through a Buchner funnel without filter paper. In some cases, where a low solubility of the active ingredient limited higher drug concentration in the final liposomal product, or where it is desired to increase the level of opioid analgesic agent initially absorbed as free opioid, the multiphase liposomal drug delivery system described and claimed in Mezei in U.S. Pat. No. 4,761,288; can be utilized to advantage. Both the base and salt forms of the active ingredient have been used for preparing the liposomal-encapsulated product.

OPIOID FORMULAS FOR INHALATION

Example 1.
Formula (for each 100 ml):

| | |
|---|---|
| Fentanyl citrate | 40.0 mg |
| Soy lecithin (unhydrogenated) | 5000.0 mg |
| Cholesterol | 500.0 mg |
| Ethanol 95% | 5.0 ml |
| Sterile water for injection | q.s. to 100.0 ml |

Example 2.
Formula (for each 100 ml):

| | |
|---|---|
| Fentanyl citrate | 60.0 mg |
| Soy lecithin (unhydrogenated) | 5000.0 mg |
| Cholesterol | 500.0 mg |
| Ethanol 95% | 5.0 ml |
| Sterile water for injection | q.s. to 100.0 ml |

Example 3.
Formula (for each 100 ml):

| | |
|---|---|
| Fentanyl citrate | 40.0 mg |
| Soy Lecithin (unhydrogenated) | 2000.0 mg |
| Cholesterol | 200.0 mg |
| Ethanol 95% | 5.0 ml |
| Sterile water for injection | q.s. to 100.0 ml |

Example 4.
Formula (for each 100 ml):

| | |
|---|---|
| Fentanyl (based) | 40.0 mg |
| Soy ecithin (hydrogenated) | 2,000.0 mg |
| Cholesterol | 200.0 mg |
| Ethanol 95% | 10.0 ml |
| Sterile water for injection | q.s. to 100.0 ml |

Example 5.
Formula (for each 100 ml):

| | |
|---|---|
| Fentanyl citrate | 60.0 mg |
| Soy lecithin (hydrogenated) | 5,000.0 mg |
| Cholesterol | 500.0 mg |
| Ethanol 95% | 5.0 ml |
| Sterile water for injection | q.s. to 100.0 ml |

Example 6.
Formula (for each 100 ml):

| | |
|---|---|
| Alfentanil HCl | 200.0 mg |
| Soy lecithin (hydrogenated) | 5,000.0 mg |
| Cholesterol | 1,000.0 mg |
| Sterile water for injection | q.s. to 100.0 ml |

Example 7.
Formula (for each 100 ml):

| | |
|---|---|
| Sufentanil | 10.0 mg |
| Soy lecithin (hydrogenated) | 2,000.0 mg |
| Cholesterol | 200.0 mg |
| Ethanol 95% | 10.0 ml |
| Sterile water for injection | q.s. to 100.0 ml |

-continued

Example 8.
Formula (for each 100 ml):

| | |
|---|---|
| Morphine | 400.0 mg |
| Soy lecithin (hydrogenated) | 7,000.0 mg |
| Cholesterol | 1,000.0 mg |
| Ethanol 95% | 10.0 ml |
| Sterile saline solution | q.s. to 100.0 ml |

PHARMACOKINETIC EVALUATIONS

Apart from drowsiness, nausea and vomiting which are known side effects of opioids, none of the subjects had any complications during the pharmacokinetic study reported below. The oxygen saturation of the subjects was maintained above 85% during the study while breathing room air. There were no significant hemodynamic changes during the study.

EXAMPLE 9

Liposome-Encapsulated Fentanyl

Ten healthy volunteers were recruited to study the plasma opioid concentration-time profiles of several liposome formulations of entanyl (Examples 1, 3, and 4) administered through the pulmonary system by inhalation. None of the studied subjects had a history of cardiovascular, respiratory, hepatic or renal dysfunction. Subjects with a history of analgesic abuse, opioid addition, or opioid allergies were excluded. Volunteers fasted for 5 hours prior to the study. Studies were conducted in a post-anesthetic care unit with monitoring of blood pressure, heart rate and pulse oximetry. A 16 gauge intravenous catheter was inserted under local anaesthesia to facilitate blood sampling. During Phase I of the study, each volunteer received an intravenous injection of 200 μg of fentanyl, insolution form (Sublimaze ™, Janssen Pharmaceutica, New Jersey), over one minute through a 21 gauge butterfly needle in the contralateral forearm. Venous blood samples (3 mls each) were drawn at 2, 4, 6, 8, 10, 15, 20, 25, 30, 60, 90, and 120 minutes and at 4, 6, 8, 12, 18, and 24 hours. The plasma was separated immediately following the blood collection and stored at −20° C. under analyzed.

Phase II of the study was conducted under similar conditions following a four-week washout period. The volunteers were divided into 3 groups: Group A (3 subjects) received the composition of Example 1; Group B (4 subjects) received the composition of Example 3; and Group C 93 subjects) received the composition of Example 4. Each volunteer received 2000 μg of liposome-encapsulated fentanyl (either Example 1, 3 or 4) in a 5 ml preparation via a nebulizer (Power Mist ™, Hospitak, Lindenhurst, N.Y., U.S.A.) with 6 $l.min^{-1}$ flow of oxygen over 15 minutes. Venous blood (3 mls) was drawn at 5, 10, 15, 20, 25, 30, 60, 90, and 120 minutes, and at 4, 8, 12, 20, 24, 32, 40, and 48 hours. The plasma was separated immediately following the blood collection and stored at −20° C. until analyzed.

All plasma fentanyl concentrations were determined using a modified radioimmunoassay (RIA) technique as described by Michiels and colleagues (Michiels M., et al: Eur J Clin Pharmacol 12: 153–158, 1977).

The plasma fentanyl concentration-time profiles of intravenous (IV) administration and via the inhalation of liposome-encapsulated fentanyl of one of three subjects in Group A (Example 1) are shown in FIGS. 1A and 1B. The illustrated fentanyl concentration-time profiles demonstrate that there are major advantages of inhaled liposome-encapsulated fentanyl over the intravenous administered fentanyl in providing pain relief. Following a bolus IV injection of 200 μg of fentanyl, there is an initial peak plasma fentanyl concentration of 4.67 $ng.ml^{-1}$ (see insert of FIGS. 1A and 1B). This peak fentanyl concentration far exceeds the reported necessary therapeutic postoperative analgesic concentrations range of 0.2 to 1.2 $ng.ml^{-1}$ Gourlay G. K., et al: Anesth Analg 67:329–37, 1988) and, has actually reached the limit which may cause respiratory depression (Glass P. S. A., et al: In Anesthesia, 3rd Edition, Miller R. E. (ed): Churchill Livingstone, New York, pp 367–88, 1990). However, due to rapid distribution and elimination, plasma fentanyl concentration ($C_{fen}$) fell below the therapeutic range (0.2 $ng.ml^{-1}$) in less than 4 hours. In other words, to obtain the benefit of only a short duration of pain relief, patients initially are exposed to a potential risk of respiratory depression following parenteral administration of opioid such as fentanyl. In contrast, following the inhalation of the liposome-encapsulated fentanyl, the peak $C_{fen}$ (1.2 $ng.ml^{-1}$) is rapidly achieved in 15 minutes (see inset of FIG. 1B) and is well below the threshold for possible respiratory depression. The plasma $C_{fen}$ is maintained within the therapeutic analgesic range for almost 24 hors which is substantially longer than obtained with IV administration (FIG. 1A).

Figure 2:
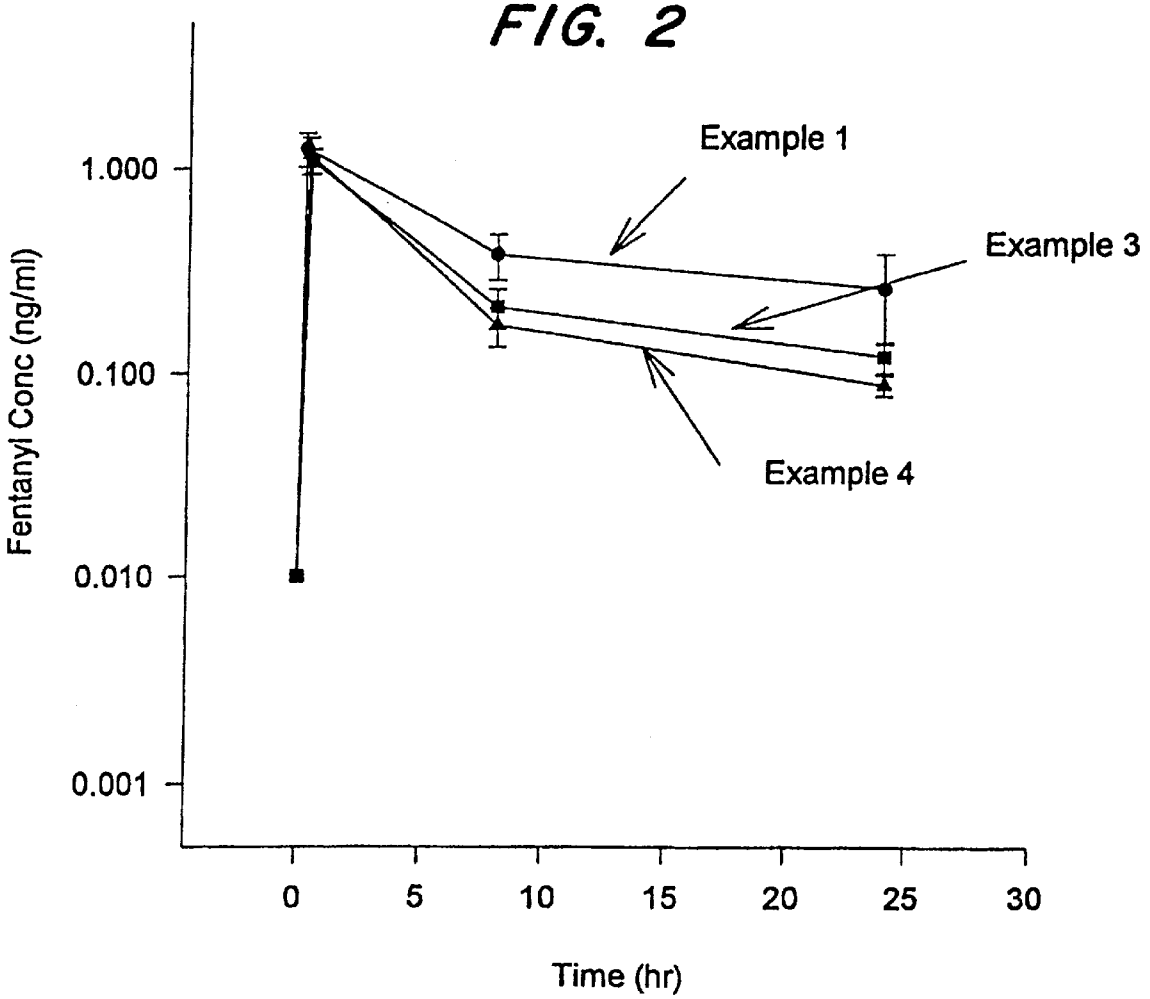
FIG. 2 graphically presents the mean or average plasma fentanyl concentrations versus time for those subjects administered the liposome compositions of Examples 1, 3, and 4 by inhalation.

The 24 hour mean (±sem) plasma fentanyl concentrations of Example 1 (3 subjects), Examples 2 (4 subjects) and Example 3 (3 subjects) are shown in FIG. 2. The formulation of Example 1 provided the best plasma fentanyl concentration profile in comparison with the other 2 formulations. The pharmacokinetic parameters following the inhalation of the 3 different formulations of liposome-encapsulated fentanyl are summarized in Table 1. Absorption of fentanyl was modest and reasonably rapid and bioavailability ranged between 8.4 to 17.5%. While Example 1 provides the highest bioavailability compared to the other two formulations, overall, the amount of opioid absorbed in each example is in good agreement with other reports on the bioavailability of drugs administered through the pulmonary system, which ranges between 10 to 20% (Tattersfield A. E.: In Bronchodilator Therapy, Clark T. J. H. (ed): ADIS Press Ltd., Auckland, New Zealand, pp 76–92, 1984).

TABLE 1

Mean (±sd) pharmacokinetic parameters following the inhalation of encapsulated fentanyl of three different liposome formulations.

| Liposome Formulation Example | Time to Peak Absorption (min) | Bio-availability | $C_{max}$ ($ng \cdot ml^{-1}$) | $T_{Max}$ (min) | $C_{fen}$ at 8 hr ($ng \cdot ml^{-1}$) | $C_{fen}$ at 24 hr ($ng \cdot ml^{-1}$) |
|---|---|---|---|---|---|---|
| 1 | 8.33 ± 2.36 | 0.175 ± 0.078 | 1.24 ± 0.398 | 15 ± 0.0 | 0.374 ± 0.16 | 0.258 ± 0.208 |

TABLE 1-continued

Mean (±sd) pharmacokinetic parameters following the inhalation of encapsulated fentanyl of three different liposome formulations.

| Liposome Formulation Example | Time to Peak Absorption (min) | Bio-availability | $C_{max}$ ($ng \cdot ml^{-1}$) | $T_{Max}$ (min) | $C_{fen}$ at 8 hr ($ng \cdot ml^{-1}$) | $C_{fen}$ at 24 hr ($ng \cdot ml^{-1}$) |
|---|---|---|---|---|---|---|
| 3 | 22.5 ± 4.33 | 0.084 ± 0.008 | 1.08 ± 0.258 | 28 ± 4.69 | 0.209 ± 0.08 | 0.120 ± 0.036 |
| 4 | 15 ± 8.165 | 0.125 ± 0.043 | 1.16 ± 0.411 | 23.33 ± 2.36 | 0.17 ± 0.064 | 0.088 ± 0.017 |

$C_{max}$ = Peak plasma fentanyl concentration.
$T_{max}$ = Time to peak plasma fentanyl concentration.

EXAMPLE 10

Liposome-Encapsulated Alfentanil

On separate occasions and under similar conditions as described above, a healthy volunteer received an intravenous injection of 500 μg of alfentanil, in solution form (Alfenta ™, Janssen Pharmaceutica, New Jersey), over one minute and 5 ml (4.0 mg) of liposome-encapsulated alfentanil (Example 6) via a nebulizer (Power Mist ™, Hospitak, Lindenhurst, N.Y., U.S.A.) with 6 $l.min^{-1}$ flow of oxygen over 15 minutes. Venous blood (3 mls) was collected at regular intervals as described above. The plasma was separated immediately following the blood collection and stored at −20° C. until analyzed. All plasma alfentanil concentrations were determined using a modified radioimmunoassay (RIA) techniques as described by Michiels and colleagues (Michiels M., et al: J Pharm Pharmacol 35:86–93, 1983).

Figures 3A, 3B:
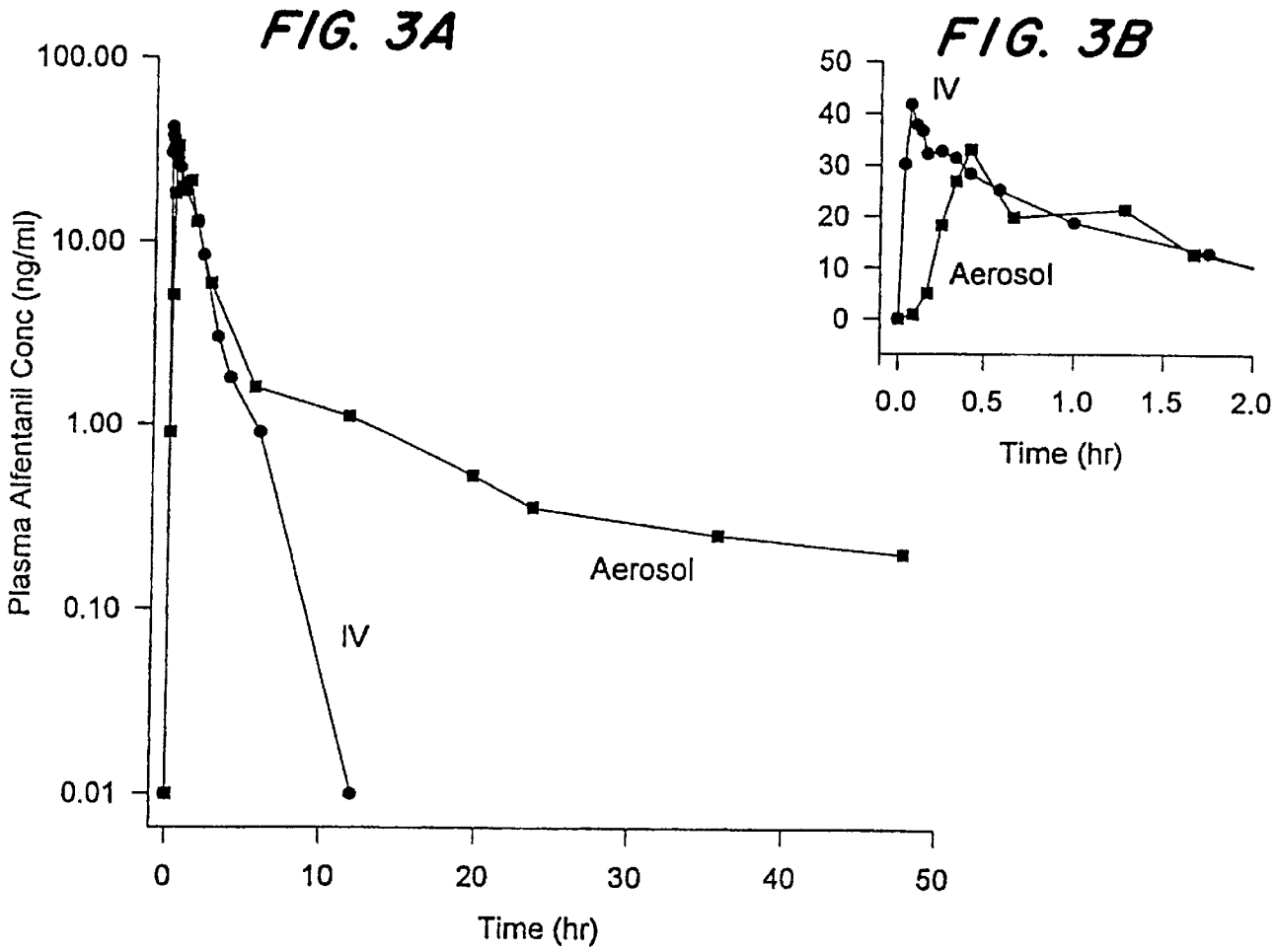
FIGS. 3A and 3B graphically present the plasma alfentamil concentrations versus time resulting from both intravenous administration and inhalation administration as described in Example 10.

The plasma alfentanil concentration-time profiles following both IV and aerosol administration are shown in FIGS. 3A and 3B. Following the IV administration, the plasma alfentanil concentration peaks rapidly. This is followed by a characteristic rapid decline of alfentanil concentration secondary to its rapid clearance by the body. The concentration of alfentanil is undetectable beyond 12 hours following the IV administration. In contrast, alfentanil concentration peaks within 25 minutes following the inhalation of liposome-encapsulated alfentanil. The plasma alfentanil is maintained substantially higher within the therapeutic analgesic range for a significantly longer period than the IV administration.

PHARMACODYNAMIC EVALUATIONS

EXAMPLE 11

Figure 4:
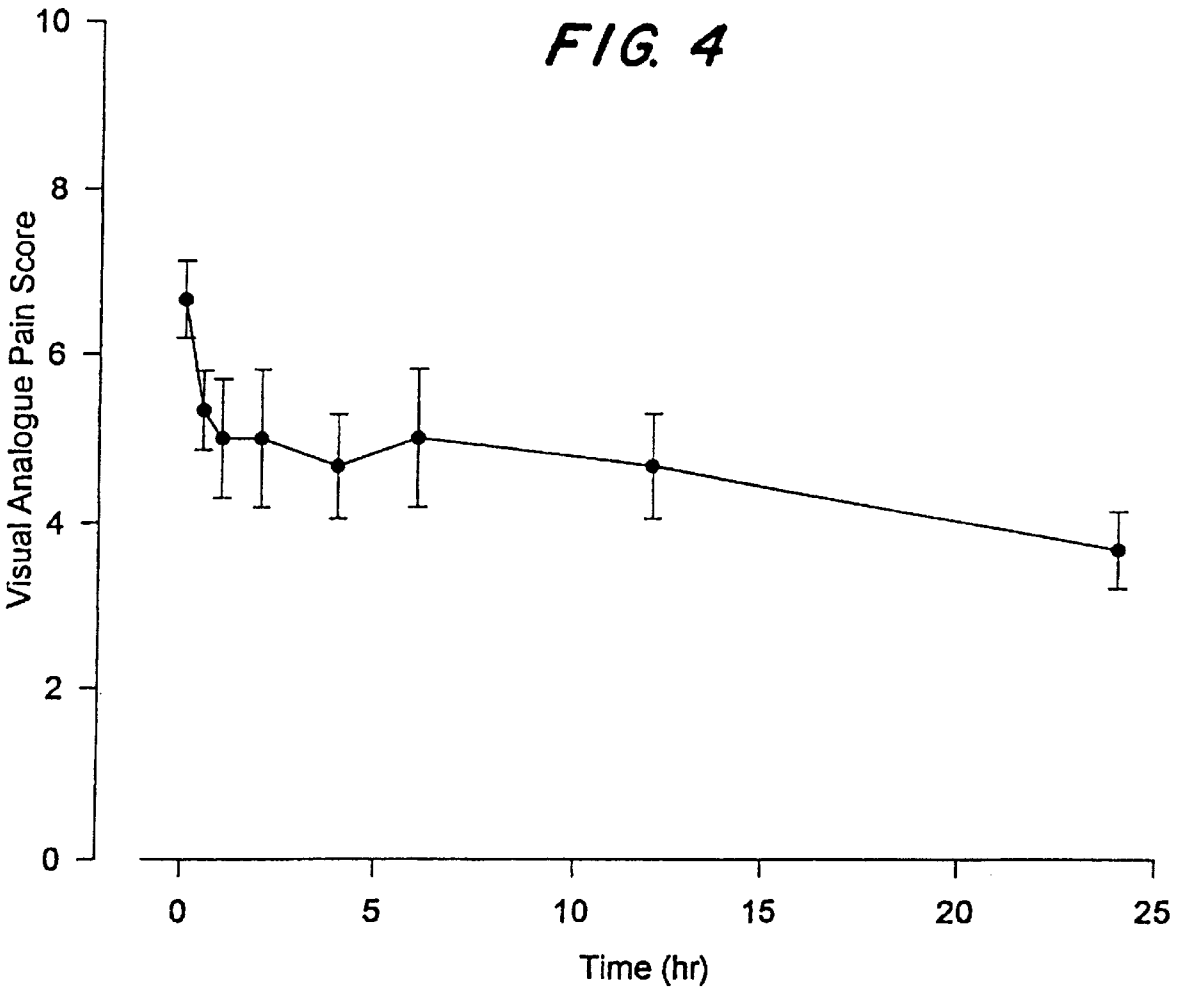
FIG. 4 graphically presents the mean or average visual analogue pain score resulting from the inhalation administration of fentanyl as described in Example 11.

Following the pharmacokinetic study with healthy volunteers, a clinical study was conducted to determine the effectiveness of inhaled liposome-encapsulated fentanyl for post-operative pain control. Three patients having lumbar discectomy under a standardized anesthetic technique were studied. When pain medication was first requested, each patient received 3000 μg of liposome-encapsulated fentanyl (Example 5) aerosol in the post anesthetic care unit following the operation. The opioid analgesic requirement and frequent visual analogue pain scores for the first 24 hours following the surgery were recorded. The average 24 hour morphine requirement following the liposome-encapsulated fentanyl aerosol was 18 (±10.4) mg which is substantially less than patients who had a similar operation but die not receive the fentanyl aerosol. Most patients required approximately 10 mg of morphine every 4 hours (60 mg for the first 24 hours) following the lumbar spine operation. Following the administration of the liposome-encapsulated fentanyl, the visual analogue pain score was also reduced from an average baseline score of 6.7 (prior to the administration of aerosol fentanyl) to a mean score of less than 5 for 24 hours (FIG. 4). The reduction in the first 24 hour post-operative opioid analgesic requirement as well as the lower visual analogue pain scores following the aerosol suggest that pulmonary route of administering liposome-encapsulated fentanyl provides an effective method of drug delivery of opioid.

On two separate occasions, liposome-encapsulated sufentanil (Example 7 which contains 500 μg of sufentanil in 5 ml) and morphine (Example 8 which contains 200 mg of morphine in 5 ml) were administered to a patient with multiple painful joints secondary to rheumatoid arthritis. Following, the administration of the liposome-encapsulated opioid, there was a significant reduction in the visual analogue pain score as well as the analgesic requirement for up to 48 hours in comparison with the baseline. These results confirmed the data obtained from fentanyl study that inhalation of liposome-encapsulated opioid provides a rapid onset and sustained relief of pain.

In summary, our preliminary pharmacodynamic data show that inhalation of liposome-encapsulated opioid is safe and efficacious in providing pain relief to patients who are suffering from both acute and chronic pain.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method of managing pain in a patient comprising administering to said patient a composition containing a liposome-encapsulated opioid analgesic agent through said patient's pulmonary system.

2. The method of claim 1 in which the liposome-encapsulated opioid analgesic agent comprises multilamellar lipid vesicles.

3. The method of claim 1 wherein the liposome-encapsulated opioid analgesic agent comprises unilamellar lipid vesicles.

4. The method of claim 1 wherein the liposome-encapsulated opioid analgesic agent is multivesicular.

5. The method of claim 1 wherein the liposome-encapsulated opioid analgesic agent comprises a multiphase liposomal system.

6. The method of claim 1 wherein the liposome-encapsulated opioid analgesic agent is prepared using a phospholipid.

7. The method of claim 6 wherein the phospholipid is selected from the groups consisting of phosphatidylcholines, lysophosphatidylcholines, phosphatidylserines, phosphatidylethanolamines, phosphatidylinositols and mixtures thereof.

8. The method of claim 6 wherein said phospholipid is provided in admixtures with a modifying agent selected from the group consisting of cholesterol, stearyl amines, stearic acid, tocopherols, and mixtures thereof.

[9. The method of claim 8 wherein said opioid analgesic agent is selected from the group consisting of alfentanil, anileridine, codiene, diamorphine, fentanyl, hydrocodone, hydromorphone, meperidine (pethidine), morphine, oxycodone, oxymorphone, propoxyphene, sufentanil, pentazocine and nalbuphine.]

10. The method of claim 1 wherein the composition contains said opioid in an amount of between 0.005% to 10% by weight.

11. A method for providing systemic analgesia in a patient by administering [a liposomal] *both a free and liposome-*encapsulated opioid analgesic agent by inhalation through said patient's pulmonary system*, said analgesic agent being selected from the group consisting of fentanyl, alfentanil and sufentanil.*

*12. The method of claim 1 wherein the opioid analgesic agent is fentanyl or a salt form thereof.*

*13. The method of claim 12 wherein the opioid analgesic is fentanyl base.*

*14. The method of claim 12 wherein the opioid analgesic is fentanyl citrate.*

*15. The method of claim 1 wherein the opioid analgesic is alfentanil or a salt form thereof.*

*16. The method of claim 15 wherein the opioid analgesic is alfentanil base.*

*17. The method of claim 15 wherein the opioid analgesic is alfentanil HCl.*

*18. The method of claim 1 wherein the opioid analgesic is sufentanil.*

*19. The method of claim 2 wherein the free form selected opioid analgesic agent is in the range of 10–20% of opioid dose.*

*20. The method of claim 2 wherein the selected analgesic agent is fentanyl citrate.*

*21. The method of claim 1 wherein the opioid analgesic agent is selected from the group consisting of fentanyl, alfentanyl and sufentanil.*

*22. A method of managing pain in a patient comprising administering to said patient a composition containing both free and liposome-encapsulated fentanyl citrate through said patient's pulmonary system, wherein said liposome-encapsulated fentanyl citrate is prepared using a phosphatidylcholine in admixture with cholesterol, and wherein said liposome-encapsulated fentanyl citrate comprises a mixture of unilamellar vesicles and multilamellar vesicles.*

*23. The method of claim 22, wherein the composition comprises an amount of fentanyl citrate suitable to afford a plasma concentration in a range of between 0.2 ng/ml to about 1.2 ng/ml.*

*24. A method for providing systemic analgesia in a patient by administering both free and liposome-encapsulated fentanyl citrate by inhalation through said patient's pulmonary system, wherein said liposome-encapsulated fentanyl citrate is prepared using a phosphatidylcholine in admixture with cholesterol, and wherein said liposome-encapsulated fentanyl citrate comprises a mixture of unilamellar vesicles and multilamellar vesicles.*

*25. The method of claim 24, wherein the composition comprises an amount of fentanyl citrate suitable to afford a plasma concentration in a range of between about 0.2 ng/ml to about 1.2 ng/ml.*

* * * * *

UNITED STATES PATENT AND TRADEMARK OFFICE

CERTIFICATE OF CORRECTION

PATENT NO. : RE 38,407 E
DATED : January 27, 2004
INVENTOR(S) : Mezei et al.

It is certified that error appears in the above-identified patent and that said Letters Patent is hereby corrected as shown below:

Column 10,
Line 2, after “containing” insert -- both --; after “a” (second occurrence) insert -- free and --.

Signed and Sealed this

First Day of June, 2004

JON W. DUDAS
*Acting Director of the United States Patent and Trademark Office*

UNITED STATES PATENT AND TRADEMARK OFFICE

CERTIFICATE OF CORRECTION

PATENT NO. : RE 38,407 E
DATED : January 27, 2004
INVENTOR(S) : Mezei et al.

It is certified that error appears in the above-identified patent and that said Letters Patent is hereby corrected as shown below:

Title page,
Item [12], please delete "Mezel et al." and insert -- Mezei et al --.
Item [75], Inventors, please delete "Michael Mezel, Nova Scotia (CA);" and insert -- Michael Mezei, Nova Scotia (CA); --

Signed and Sealed this

Twenty-seventh Day of July, 2004

JON W. DUDAS
*Acting Director of the United States Patent and Trademark Office*